US009486482B2

(12) United States Patent
Chaudhary et al.

(10) Patent No.: US 9,486,482 B2
(45) Date of Patent: Nov. 8, 2016

(54) HERBAL COMPOSITION FOR TREATING MALE SEXUAL DYSFUNCTION

(71) Applicants: ENOVATE BIOLIFE PRIVATE LIMITED, Mumbai (IN); ENOVATE BIOLIFE LLC, Wilimington, DE (US)

(72) Inventors: Latha Chaudhary, Mumbai (IN); Rekha Patel, Mumbai (IN); Mughda Kulkarni, Mumbai (IN); Navneet Sonawane, Mumbai (IN)

(73) Assignee: Enovate Biolife Private Limited, Mumbai (IN)

( * ) Notice: Subject to any disclaimer, the term of this patent is extended or adjusted under 35 U.S.C. 154(b) by 76 days.

(21) Appl. No.: 14/304,455

(22) Filed: Jun. 13, 2014

(65) Prior Publication Data

US 2014/0294998 A1 Oct. 2, 2014

Related U.S. Application Data

(63) Continuation of application No. 13/016,079, filed on Jan. 28, 2011, now abandoned.

(30) Foreign Application Priority Data

May 6, 2009 (IN) .......... 1380/MUM/2009
Jan. 29, 2010 (IN) .......... 1380/MUM/2009

(51) Int. Cl.
| | |
|---|---|
| A61K 36/185 | (2006.01) |
| A61K 36/81 | (2006.01) |
| A61K 36/67 | (2006.01) |
| A61K 35/04 | (2006.01) |
| A61K 36/19 | (2006.01) |
| A61K 36/28 | (2006.01) |
| A61K 36/48 | (2006.01) |
| A61K 36/896 | (2006.01) |
| A61K 36/8965 | (2006.01) |

(52) U.S. Cl.
CPC ............ *A61K 35/04* (2013.01); *A61K 36/185* (2013.01); *A61K 36/19* (2013.01); *A61K 36/28* (2013.01); *A61K 36/48* (2013.01); *A61K 36/67* (2013.01); *A61K 36/81* (2013.01); *A61K 36/896* (2013.01); *A61K 36/8965* (2013.01)

(58) Field of Classification Search
CPC ..... A61K 36/185; A61K 36/81; A61K 36/67
USPC ...................... 424/725.1, 760, 725
See application file for complete search history.

(56) References Cited

U.S. PATENT DOCUMENTS

| | | | | |
|---|---|---|---|---|
| 6,080,401 | A | * | 6/2000 | Reddy .............. A61K 36/235 424/725 |
| 7,014,872 | B2 | * | 3/2006 | Pushpangadan ...... A23L 1/3002 424/725 |
| 2003/0152650 | A1 | | 8/2003 | Kang et al. |
| 2003/0185913 | A1 | * | 10/2003 | Pushpangadan ...... A23L 1/3002 424/739 |
| 2005/0208158 | A1 | | 9/2005 | Alexiev |
| 2006/0062863 | A1 | * | 3/2006 | Ghosal .............. A23F 3/14 424/757 |
| 2006/0269623 | A1 | | 11/2006 | Swaab |

FOREIGN PATENT DOCUMENTS

| | | |
|---|---|---|
| WO | 0002573 | 1/2000 |
| WO | 03070262 | 8/2003 |
| WO | 03094944 | 11/2003 |

OTHER PUBLICATIONS

Cannell Natural Products Isolation; Humana Press, Inc. Totowa, NJ (1998) pp. 348 and 349.*
Fetrow et al. The Complete Guide to Herbal Medicines; Simon & Schuster, Inc., New York, NY, (2000), pp. 3, 8 and 9.*
Mann, D. Natural Alternatives to Viagra; Better Nutrition; 60 (12) Dec. 1998:16 2 pages from ProQuest Database.*
Scgara, Rasayoga, Hariprapanna J vol. I, Krishnadas Academy, Varanasi, Edn. Reprint 1999, p. 497 (3 page translation, printed from Traditional Knowledge Digital Library, India (TKDL).*
Bherata Bhaiaja Ratnekara, vol. IV: B. Jain Publishers, New Delhi, Second Ed. 1999, p. 497 (3 page translation from TKDL provided).*
Hindustena C Vaidyareja, Ramesh Vihal Rughuvan, Gajenana book depot, Mumbai, Aug. 15, 1973, pp. 176-177 (3 page translation from TKDL provided).*
Burnett, et al., "The Role of Nitric Oxide in Erectile Dysfunction: Implication for Medical Therapy", The Journal of Clinical Hypertension. Supp. 4 vol. 8 No. 12 Dec. 2006, pp. 53-62.
Delvin, et al., "Lack of Sex Drive in Men (lack of Libido)", http://www.netdoctor.co.uk/sex_relationships/facts/malelacksexdrive.htm; [viewed online Sep. 13, 2013].
Fetrow, et al., "The Complete Guide to Herbal Medicines", Simon & Schuster, Inc. New York, NY, (2000), pp. 3, 8 and 9.
Kolodny, et al., "Sexual Dysfunction in Diabetic Men", Diabetes. vol. 23, No. 4 pp. 306-309. Apr. 1974.
Mann, "Natural Alternatives to Viagra", Better Nutrition; 60 (12) Dec. 1998; 16.
Montgomery, "Sexual Desire Disorder", Psychiatry (Edgmont). Jun. 2008; 5(6): 50-55.
Yuan, et al., "Sexual function of premature ejaculation patients assayed with Chinese Index of Premature Ejaculation", Asian J. Androl Jun. 6, 2004: 121-126 ([http://www.asiaandro.com/archive/1008-682X/6/121.html]; viewed online Sep. 13, 2013).
Zitzmann, et al., "Association of Specific Symptoms and Metabolic Risks with Serum Testosterone in Older Men", The Journal of Clinical Endocrinology & Metabolism, Nov. 2006, 91(11): 4335-4343.

(Continued)

*Primary Examiner* — Chris R Tate
(74) *Attorney, Agent, or Firm* — Kramer Amado P.C.

(57) ABSTRACT

Disclosed herein is synergistic herbal composition comprising extracts of herbal ingredients of *Tribulus terrestris, Withania somnifera, Curculigo orchioides, Mucuna pruriens, Asparagus adscendens, Asteracantha longifolia, Asphaltum*, and optionally the extracts of *Piper longum* and *Anacyclus pyrethrum* for the treatment of disorders associated with Male Sexual Dysfunction.

16 Claims, 4 Drawing Sheets

(56) References Cited

OTHER PUBLICATIONS

Mohammad Najmul Ghani Khan, Khazaain-al-Advia vol. III (20th century AD), 05 (p. 4-8) (Ref. p. No. of publication: 858), 1926 AD, Nadeem Yunus Printer/Sheikh Mohd Basheer & Sons, Lahore.

Mohammad Najmul Ghani Khan, Khazaain-al-Advia vol. III (20th century AD), 05 (p. 9-13) (Ref. p. no. of publication: 875), 1926 AD, Nadeem Yunus Printer/Sheikh Mohd Basheer & Sons, Lahore.
Govinda Dasa, Bhaisajya Ratnavali—Edited by Rajeshvaradutta Shastri, 06 (p. 14-19) (Ref. p. no. of publication: 792 ), Edn. 14th, 2001, Chaukhamba Sanskrit Sansthan, Varanasi, India.

\* cited by examiner

HERBAL COMPOSITION FOR TREATING MALE SEXUAL DYSFUNCTION

CROSS-REFERENCE TO RELATED APPLICATIONS

This application is a continuation of parent U.S. application Ser. No. 13/016,079, filed on Jan. 28, 2011. The entire disclosure of the prior application is hereby incorporated by reference in its entirety.

FIELD OF INVENTION

This invention relates to synergistic herbal composition useful for treating symptoms associated with Male Sexual Dysfunction or to improve Male Sexual Function. More particularly, the present invention relates to the synergistic combination of the ingredients derived from natural sources preferably plants and minerals which are useful for treating disorders associated with male sexual dysfunction.

BACKGROUND OF THE INVENTION

One's sexual functioning is not only an expression of reproductive capacity and gender identity but also serves a major role in cementing the emotional bond with primary partner. When this capacity is diminished or disrupted, the psychological implications can range from minor to catastrophic, depending upon the individual history & situation. Therefore treatment of sexual dysfunction is imperative as it can have a profound effect on the well-being of the individual.

Thus, sexual dysfunction has considerable importance and form the subject of intensive biomedical research efforts. According to recent statistics, the problem of impotence in its various forms (such as absence or loss of libido, erectile dysfunction and premature ejaculation) affects some 70% w/w of the population aged approximately 50 and over.

Male sexual dysfunction can be caused by physical or psychological stress. Sexual dysfunction may be of any one of following type:
Loss of libido
Erectile dysfunction
Premature ejaculation
Delayed or inhibited orgasm
Physical abnormalities of the penis Treatment for Male Sexual Dysfunction:

Male sexual dysfunction is generally the combination of one or more of above mentioned symptoms. Thus the approach of the therapy should be to treat all the symptoms simultaneously, till today most of the available measures aim to target only one or two aspects of sexual dysfunction and not to improve overall sexual life.

Various aspects of treatments have been suggested for male sexual dysfunction associated disorders as exemplified below.

Depression or anxiety disorders may need treatment.
Any physical problems that may be affecting sexual function should be addressed.
If a medication is interfering with sexual function, it may be possible to change or discontinue the medication.
Prescription medications that treat erectile dysfunction may help a man to achieve and maintain erections.
Hormonal treatment, such as testosterone replacement therapy, may help with hormone imbalances that are contributing to sexual dysfunction.
For psychological causes of sexual dysfunction, such as relationship problems may be treated beneficially by counseling, either individually or as a couple.
Sexual therapy with a therapist who specializes in sexual dysfunction may also help to resolve the problems.
In obese men with erectile dysfunction, weight loss and increased physical activity are associated with an improvement in erectile function in about one third of patients Therapy of men with erectile dysfunction is aimed at restoration of the two vital sexual functions: the capacity to acquire and sustain penile erections; and the reactivation of libido. Optimal treatment varies with the cause of the erectile dysfunction (Tables 2A-2B): Phosphodiesterase-5 (PDE-5) inhibitors, penile self-injection programs with vasoactive drugs, vacuum erection devices, or penile prostheses allow many men with vasculogenic, neurogenic, or psychogenic erectile dysfunction to acquire and maintain erections.

Oral treatments for male sexual dysfunction (Table 2 A)

| Medication | Mechanism | Pros and cons | Dosing |
|---|---|---|---|
| Sildenafil (Viagra ®) | Inhibits enzyme phosphodiesterase 5, allowing cyclic GMP to accumulate within penis | 100 mg effective in 75 percent of men. Side effects: headaches, dyspepsia, vasodilation, diarrhea and blue tinge to vision. Contraindicated if using nitrates. | Taken one hour before sex and effective up to four hours. Stimulation needed for erection. Dose: 25 to 100 mg |
| Vardenafil (Levitra) | Same as sildenafil | Similar efficacy/side effects to sildenafil, but no visual side effects. | Similar onset and duration of action as sildenafil. Dose: 2.5 to 20 mg |
| Tadalafil (Cialis) | Same as sildenafils | Similar efficacy/side effects to sildenafil, but no visual side effects. | Similar onset of action as sildenafil. Duration of action is up to 36 hours. Dose: 2.5 to 20 mg |
| Yohimbine | Blocks presynaptic alpha-2 receptors. Stimulates mid-brain, increases libido. Might increase local blood flow, decreases outflow. | Used for psychogenic ED. May have placebo effect. Alternative to testosterone for libido. Anxiety and insomnia are side effects. May increase labile hypertension. | 5.4 mg TID |

-continued

Oral treatments for male sexual dysfunction (Table 2 A)

| Medication | Mechanism | Pros and cons | Dosing |
|---|---|---|---|
| Trazodone | Alpha blocker component. May cause priapism. | Used for psychogenic ED. Treats depression. Dizziness, lethargy are side effects. | 50-100 mg/day |

Suppositories, injections, and devices for sexual dysfunction (Table 2B)

| Treatment | Effect | Pros and cons | Usage pattern |
|---|---|---|---|
| Suppository-MUSE (alprostadil) | Alprostadil (prostaglandin E1) in gel form delivered by applicator into meatus of penis. | Can be used twice daily. Not recommended with pregnant partners. | Inserted 5-10 minutes before sex. Effects last 1 hour. |
| Alprostadil (Caverject and Edex) | Prostaglandin E1 injected into base of penis. Causes smooth muscle relaxation in corpus cavernosae. | Effective in 50 to 85 percent of cases. May be painful and not recommended for daily use. Priapism occurs uncommonly. | Inject 10-20 minutes before sex. Erections may last over an hour. |
| Invicorp (VIP and phentolamine) | Peptide, VIP and alpha-blocker, phentolamine causes relaxation of penile vascular smooth muscle. | Possibly more effective than alprostadil. Causes less pain. Priapism rare. | Inject 10-20 minutes before sex. Requires stimulation to have erection. |
| Device-Vacuum pump | Removes air from chamber over penis, creating a vacuum and drawing blood into penile cavernosae. Elastic tourniquet at base holds blood in penis. | One-time expense. Safe if erection not maintained more than one hour. May not be acceptable to partner. Penis is hinged at base. May interfere with ejaculation. | Inflated just before sexual activity. Erection lasts until elastic ring removed. |

Recently, research has been done on Erectile Dysfunction and Sildenafil has been made available for patients, but it has shown to provide benefit only to patients with Erectile Dysfunction but not for other parameters like loss of libido and premature ejaculation. It is also contradicted in patients who are taking nitrates. The adverse events associated with these drugs are sudden decrease or loss of hearing & vision. The most common side effects of these medications are headache, facial flushing, and upset stomach. Less commonly, bluish vision, blurred vision, or sensitivity to light may briefly occur.

US 2003/0152650 discloses pharmaceutical composition for the prevention and treatment of premature ejaculation and/or hypersensitivity of sexual stimulation is provided. The composition contains purified sumsoo extract and purified ginseng extract containing saponin as the main component, without other herbal essential oil components.

US 2006/0269623 teaches about herbal compositions and methods of treatment for prevention or treatment of erectile dysfunction disorders and ameliorating symptoms thereof and as a preventative measure against erectile dysfunction. The methods comprise administering a therapeutically effective composition of matter comprising the following herbal and other components: Herba cynomorii, Rhizhomnas atractylodis macrocephalae, Radix rehmannia glutinosea longui, Herba epimedii, Fructus lycii, Fructus schisandrae chinensis, Radix poloygoni multiflor, Cortex cinnamonia cassiae, Fructus amoni, and Radix ginseng.

WO 03/094944 discloses a pharmaceutical composition which are useful in the treatment of male and female sexual dysfunction comprising extracts of *Tribulis teristris, Epimedium koreanum, Cinnamonon cassia* in the weight ratio of 1.5-3.5:1-2:0.1-0.4, respectively; and optionally arginine or a physiologically equivalent ester, salt or precursor thereof and a suitable carrier or excipients. The increase in sexual activity can only be obtained by using the extracts of the various plants with the said precise ratio.

WO 2000/002573 describe about composition and method for treating sexual dysfunction by natural means using a combination of L-arginine, ginseng and Zizyphi fructus in an orally administered dosage. The combination works synergistically to alleviate erectile dysfunction by stimulating enough release of NO in the corpus cavernosum to produce and sustain smooth muscle relaxation, thereby allowing the inflow of blood and alleviating erectile dysfunction. Thus, a natural medicinal alternative to Viagra (Sildenafil) is provided for the treatment of erectile dysfunction. The composition and method is also useful in treating sexual conditions in females.

Various other devices such as vacuum devices, penile implants are available, but benefit only those patients whose function has been severely impaired. Bruising, skin breakdown, and penile pain may occur while using these devices.

It is evident from the prior arts that existing treatments for male sexual dysfunction have side effects or are not very comfortable for usage. These treatments do not show effect on all aspects of Male Sexual Dysfunction. There is therefore a need in the art to provide a product which is safe and treats various aspects of Male Sexual Dysfunction such as erectile dysfunction, quality of erection, premature ejaculation, libido levels, orgasmic function, satisfaction ratings for sexual intercourse and the frequency of sexual intercourse.

Therefore, the instant invention aims to provide synergistic combination of the ingredients derived from natural sources preferably plants and minerals to treat the above aspects of male sexual dysfunction simultaneously without considerable side effects.

Various herbs that can be used for the purpose of the present invention to treat various aspects of sexual dysfunction are described below:

*Tribulus terrestris* (Gokshur)

Gokshur is a plant-based drug used as an aphrodisiac, a diuretic, and has proven useful in the treatment of urolithiasis, dysurea, impotence, and kidney dysfunction.

*Withania somnifera* (Ashwagandha)

Ashwagandha has been used for thousands of years as a popular remedy for many conditions. Perhaps its main use, as described in Ayurvedic literature, is as a "rasayana" or rejuvenating drug. The word Ashwagandha indicates the equine (of horses) odor of the plant. Ashwagandha is one of the best known and most researched Ayurvedic herbs and holds a place in the Ayurvedic traditions similar to Ginseng in Chinese therapies. For that reason, *Withania somnifera* is often referred to as the "Indian Ginseng". *Withania somnifera* is used in several indigenous drug preparations for maintaining health as well as treatment of several disease conditions.

*Asparagus adscendens* (Safed Musali)

Safed Musli is one of the chief ingredients in Ayurveda and other local folklore medicines for ages. The dried roots of Safed Musli (*Asparagus adscendens*) are used in Unani medicine as an aphrodisiac as they are rich in glycosides. Safed Musli offers significant protection against stress induced changes. It cures many physical illness and weakness and for increasing general body immunity. Safed Musli is used for the preparation of health tonic that is used in general weakness and debility.

*Mucuna pruriens* (Kawach)

It is considered as one of the most effective aphrodisiac, also used in treatment of liver and gall bladder disorders. *Mucuna pruriens* seeds have also proven to be effective in profuse menstruation. Kawach is extensively used to treat Parkinsonism and diabetes.

*Mucuna pruriens* is a widely available Indian herb with seeds having wonderful therapeutic properties. The seeds due to the presence of L-DOPA and nicotine are in great demand. L-DOPA is a neurotransmitter precursor, and is effective for relief in Parkinson's disease. Seeds of Mucuna pruriens are prescribed in the form of powder in the treatment of leucorrhoea, spermatorrhoea, and in cases requiring aphrodisiac action Seed powder including seed coat is an ingredient of the ayurvedic drug Vita-ex given as an aphrodisiac. It is prophylactic against oligospermia and is useful in increasing sperm count, ovulation in women, etc. It prevents male and female sterility and acts as a nervine tonic. *Mucuna pruriens* seeds are widely used for treating male sexual dysfunction in Unani Medicine, the traditional system of medicine of Indo-Pak sub-continent. *Mucuna pruriens* seeds are also proven to be effective in profuse menstruation and in paralysis and have been used since ancient times in the treatment of nervous disorders.

*Asteracantha longifolia* (Gokhulakanta)

This herb is a tonic and stimulant. It promotes libido. The ash of the plant serves as an excellent diuretic. The root of the plant is beneficial in the treatment of gonorrhoea and urinary disorders, including inflammation of the urinary tract and stone in the kidneys. Its decoction can be given in doses of 30 to 60 grams, twice or thrice a day. The decoction of its leaves can be used with confidence in case of syphilis and gonorrhoea. The mucilage obtained by infusing the seeds in water is also prescribed in gonorrhoea, urinary diseases and as a tonic. Chloroform extract of the leaves of *Asteracantha longifolia* may be used for haematopoietic activity in Ayurvedic system of medicine.

*Curculigo orchioides* (Kali Musali)

According to references found in Ayurveda, Kali Musali root having property of heating, aphrodisiac, alternative, appetizer, fattening and useful in treatment of piles, biliousness, fatigue, blood related disorders etc.

*Asphaltum* (Shilajit)

Shilajit has been used historically for general physical strengthening, anti-aging, blood sugar stabilization, libido, injury healing, urinary tract rejuvenation, enhanced brain functioning potency, bone healing, kidney rejuvenation, immune system strengthening, arthritis, hypertension, obesity and many other application for numerous conditions.

*Anacylus pyrethrum* (Akarkarbh)

This perennial plant, in habit and appearance like the chamomile, has stems that lie on the ground for part of their length, before rising erect.

Root of the *Anacyclus pyrethrum* is used to treat premature ejaculation. In Ayurvedic literature it is referred as "shukrastambhak dravya"

*Piper longum* (Pippali)

The botanical name of pippali is *Piper longum* and it belongs to family piperaceae. The fruits contain 1% volatile oil, resin, a waxy alkaloid, a terpenoid substance and alkaloids piperine and piperlongumine. The roots contain piperine, piperlongumine or piplartine. The seeds contain sylvatin, sesamin and diaeudesmin.

Pippali is a Rasayana plant appearing in ancient medicinal literature reputed in Ayurveda to promote physical and mental health, improve defense mechanisms of the body, and enhance longevity. This herb yields an alkaloid called Piperine. Piperine is a proven bioenhancer that increases the availability of nutritional substances. Pippali as a powerful 4:1 ratio extract stimulates thermogenic response or the release of metabolic heat energy in the body causing a noticeable "warming of the loins" as a precursor to sexual activity.

The individual ingredients discussed above of the present invention have been in use since ancient times for variety of diseases.

Many natural ingredients have been listed in the literature of traditional medicinal systems for their aphrodisiac activity. Such ingredients are available for the management of one or more symptoms of sexual dysfunction. Higher therapeutic dose of single ingredient and lack of selectiveness/effectiveness against various aspects of sexual dysfunction are again of major concerns. Many attempts in the prior art have been made to prepare the combinations of such ingredients as a remedy for overall sexual satisfaction. The drawbacks of the prior art formulations are least standardization, no impurity profiling, pesticide residues (in case if raw material from cultivated herb), variable concentration of actives, unacceptable pharmaceutical dosage form and most importantly, the lack of safety and efficacy background through preclinical and clinical studies.

The existing treatments do not show effect on all aspects of Male Sexual Dysfunction. Therefore, the instant invention provides the synergistic combination of the ingredients derived from natural sources preferably plants and minerals to treat all aspects of male sexual dysfunction simultaneously without considerable side effects. The synergistic composition of the present invention is observed to work effectively against the various sexual dysfunction.

Therefore, the objective of the present invention is to provide synergistic herbal composition useful for the treatment of various aspects of Male Sexual Dysfunction such as erectile dysfunction, loss or decreased libido, and premature ejaculation as well as to improve Male Sexual Function.

SUMMARY OF THE INVENTION

The present invention provides a synergistic herbal composition useful to improve male sexual health and also for treating symptoms associated with Male Sexual Dysfunction. It is a safe and effective blend of herbs and minerals selected from *Tribulus terrestris, Withania somnifera, Curculigo orchioides, Mucuna pruriens, Asparagus adscendens, Asteracantha longifolia, Asphaltum* and optionally *Piper longum* and *Anacyclus pyrethrum* The selective herbs used in the present invention provide the urge—the libido or desire or drive to have sex as often as patient likes. Within a few days of taking of the synergistic herbal composition of the present invention, one should gradually begin to notice a change in individual's sexual response with increasing sexual pleasure.

In one aspect, the invention provides process for preparation of composition of the invention wherein said process comprises mixing active extracts of the above herbs optionally with one or more suitable pharmaceutical carriers/excipients. The active extracts of the above herbs and excipients can be formulated into compositions and dosage forms according to methods known in the art.

In another aspect, the invention provides method for treating symptoms associated with Male Sexual Dysfunction or to improve Male Sexual Function.

In yet another aspect, the invention discloses use of the 'composition of the invention' in preparing the medicament intended to treat the subjects with different types of Male Sexual Dysfunction or to improve Male Sexual Function of the subjects.

DETAIL DESCRIPTION OF THE INVENTION

Figure 1:
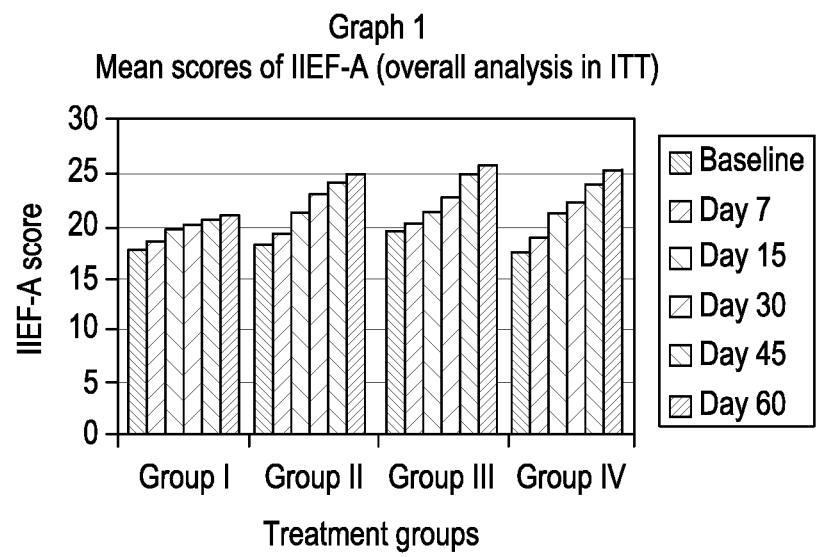
FIG. 1: is a graphical depiction of IIEF-A scores in overall analysis.
Figure 2:
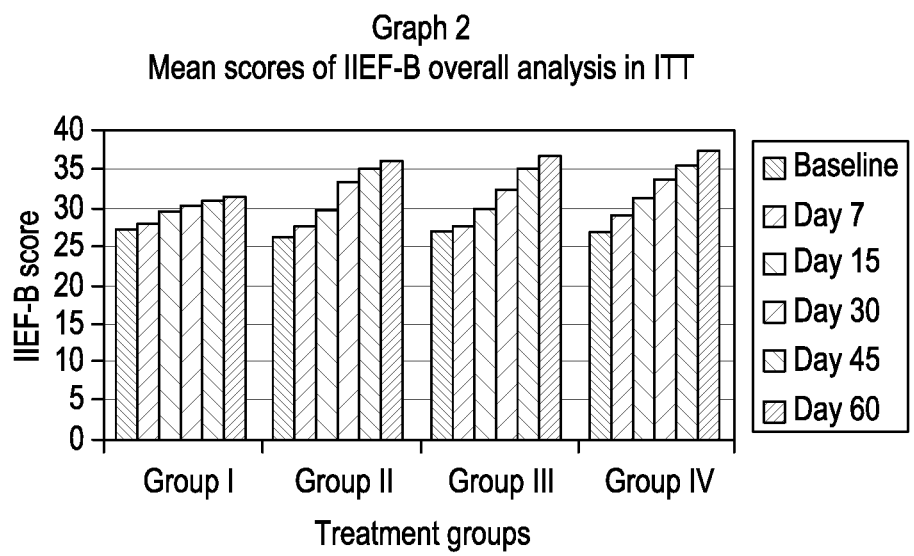
FIG. 2: is a graphical depiction of IIEF-B scores in overall analysis.
Figure 3:
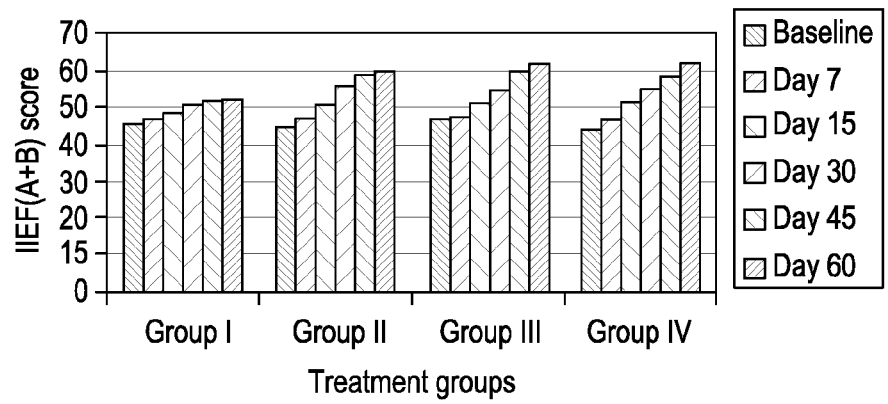
FIG. 3: is a graphical depiction of IIEF (A+B) scores in overall analysis
Figure 4:
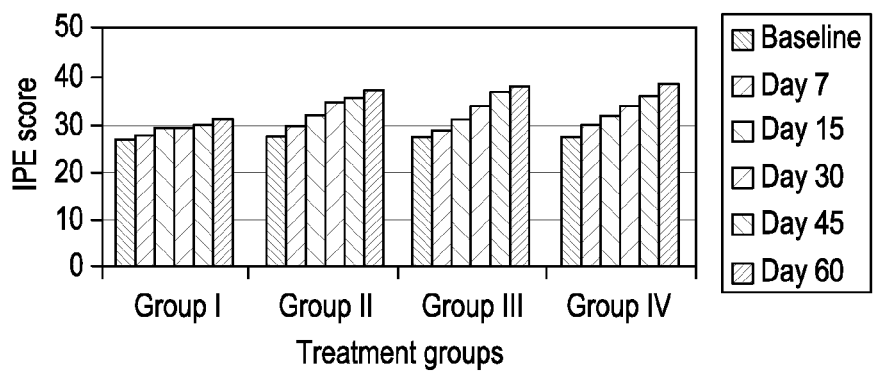
FIG. 4: is a graphical depiction of IPE scores in overall analysis.
Figure 5A:
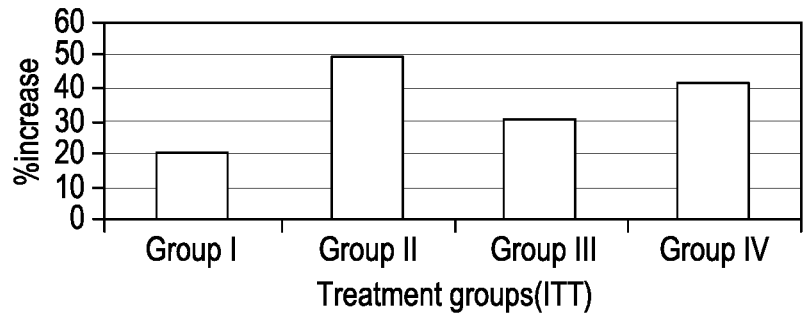
FIG. 5(*a*): is a graphical depiction of Increase in ability to get an erection to get an erection during sexual activity FIG. 5(*b*): is a graphical depiction of Increase in ability to maintain an erection after penetration FIG. 5(*c*): is a graphical depiction of Subjects not finding it difficult to maintain erection to completion of intercourse
Figure 5B:
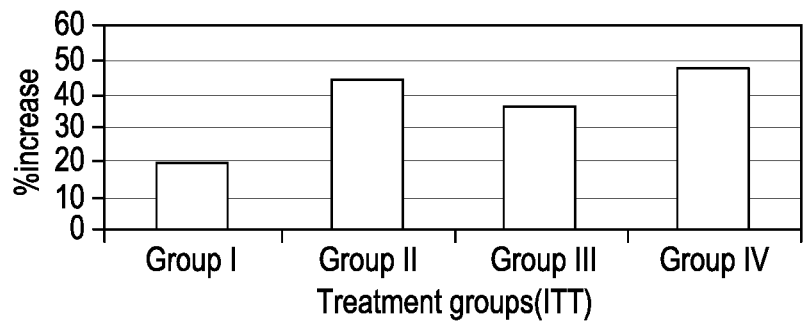
Figure 5C:
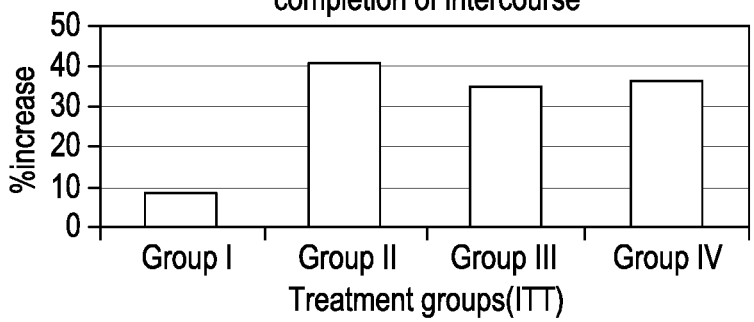

The invention will now be described in details in connection with certain preferred and optional embodiments so that various aspects thereof may be more fully understood and appreciated.

The phrase 'composition of the invention' herein means and includes the composition comprising 'herbal extracts disclosed as formulation E-MA-H as well as E-MA-HP optionally with at least one of the pharmaceutical carrier/excipients' as described according to the present invention.

Further, the seven drug combination as in formulation 1 is designated as E-MA-H and nine drug combination as in formulation 2 is designated as E-MA-HP herein below throughout the text In preferred embodiment the present invention describes synergistic herbal composition comprising extracts of *Tribulus terrestris, Withania somnifera, Asparagus adscendens, Mucuna pruriens, Asteracantha longifolia, Curculigo orchioides, Asphaltum* and optionally *Anacylus Pyrethrum* and *Piper Longum* in an effective amount useful for treating disorders associated with Male Sexual Dysfunction or to improve Male Sexual Function.

Accordingly in one of embodiment, the invention discloses the herbal composition comprising of *Tribulus terrestris* extract in an amount of about 10 to 90%; *Withania somnifera* extract in an amount of about 10 to 90%; *Curculigo orchioides* extract in an amount of about 10 to 90%; *Mucuna pruriens* extract 5 to 70%, *Asparagus adscendens* extract in an amount of about 10 to 90%, *Asteracantha longifolia* extract in an amount of about 5 to 90%, *Asphaltum* extract in an amount of about 10 to 90%, *Piper longum* extract in an amount of about 0 to 70% and *Anacyclus pyrethrum* extract in an amount of about 0 to 70% of the total formulation.

Accordingly in another embodiment, the invention discloses the herbal composition comprising of *Tribulus terrestris* extract in an amount of about 5 to 90%; *Withania somnifera* extract in an amount of about 10 to 90%; *Curculigo orchioides* extract in an amount of about 5 to 90%; *Mucuna pruriens* extract 5 to 70%, *Asparagus adscendens* extract in an amount of about 10 to 90%, *Asteracantha longifolia* extract in an amount of about 5 to 90%, *Asphaltum* extract in an amount of about 10 to 90% *Piper longum* extract in an amount of about 1 to 70% and *Anacyclus pyrethrum* extract in an amount of about 4 to 70% of the total formulation.

In another embodiment, the herbal extracts are derived from fruit, leaves, flower heads, stem, bark, root or other plant parts. Further, the herbal extract is extracted using solvents like water, alcohols and hydro-alcohols or any other organic solvents.

All the ingredients of synergistic herbal composition of the present invention are well standardized with acceptable impurity profiles. The raw materials as well as the finished product were well evaluated for their heavy metal residues which is the major concern with herbal products. All the ingredients were reported to be safe in literature; further, the product of the present invention has been proven to be safe in preclinical studies. The major evidence for the effectiveness of the composition of the present invention is the clinical study on humans in which the synergistic herbal combination of the present invention showed significant increase in overall sexual satisfaction.

The herbal extracts used in the present formulations are extracted using various parts of herbs in solvents, is described below:

Formulation 1

| Ingredients | Parts used | Solvent |
|---|---|---|
| *Tribulus terrestris* | Fruit | Alcohol 85% |
| *Withania somnifera* | Roots/Rhizomes | Hydro Alcoholic 50% |
| *Asparagus adscendens* | Roots/Rhizomes | Water |
| *Mucuna pruriens* | Seed | Water |
| *Asteracantha longifolia* | Entire plant | Water |
| *Curculigo orchioides* | Roots/Rhizomes | Water |
| *Asphaltum* | Exudate | Hydro Alcoholic 50% |

Formulation 2

| Ingredients | Part used | Solvent |
| --- | --- | --- |
| Tribulus terrestris | Fruit | Alcohol 85% |
| Withania somnifera | Roots/Rhizomes | Hydro Alcoholic 50% |
| Asparagus adscendens | Roots/Rhizomes | Water |
| Mucuna pruriens | Seed | Water |
| Asteracantha longifolia | Entire plant | Water |
| Curculigo orchioides | Roots/Rhizomes | Water |
| Asphaltum | Exudate | Hydro Alcoholic 50% |
| Anacyclus pyrethrum | root | Alcohol 70% |
| Piper longum | fruit | Alcohol 90% |

Each herbal extract was tested for heavy metals to comply with the following specifications.

Heavy Metals Profile

| | |
| --- | --- |
| Arsenic | Not more than 10 ppm |
| Lead | Not more than 10 ppm |
| Cadmium | Not more than 0.3 ppm |
| Mercury | Not more than 1 ppm |

In one of the embodiment, the invention provides process for preparation of composition of the invention wherein said process comprises mixing active extracts of the above herbs optionally with one or more suitable pharmaceutical carriers/excipients. The active extracts of the above herbs and excipients can be formulated into compositions and dosage forms according to methods known in the art.

The 'composition of the invention' is preferably administered optionally with one or more pharmaceutical excipient(s)/carrier(s). The oral administration may be accomplished by ingesting the composition preferably in a form of capsule, tablet, granules, syrup and other suitable dosage forms.

The quantity of the compound used in 'composition of the invention' will vary depending upon the body weight of the patient and the mode of administration and can be of any effective amount to achieve the desired therapeutic effect.

In yet another embodiment, the invention provides method for treating symptoms associated with different types of Male Sexual Dysfunction or to improve overall Male sexual function, wherein said method comprises administering an 'effective amount' of the 'composition of invention' according to the subject suffering from the symptoms associated with different types of Male Sexual Dysfunction or to improve Male Sexual Function of the subject. The subject mentioned herein is human.

The 'effective amount' as described above means and includes the amount required to treat/alleviate the severity of symptoms associated with this ailments as decided by the persons of ordinary skill in the art. The dosage form of the composition of the invention may vary from 1 mg to 100 mg/day/kg body weight. Preferable daily dose is in the range of one to six capsules in divided doses per day.

In yet another embodiment, the invention discloses use of the 'composition of the invention' in preparing the medicament intended to treat the subjects with different types of Male Sexual Dysfunction.

In yet another embodiment, the invention discloses use of the 'composition of the invention' in a subject in need thereof to improve Male Sexual Function or treating the subjects suffering from symptoms associated with Male Sexual Dysfunction.

Pilot Study:—

Pilot study to evaluate safety and efficacy of the present invention (formulation, E-MA-H) was carried out on subjects having Male Sexual Dysfunction.

Nine sexually active males, 25-45 years of age, with symptoms of sexual dysfunction like Erectile Dysfunction (ED), Premature Ejaculation (PE), Decreased libido & Dissatisfaction were enrolled in the study. Subjects were screened for Thyroid Stimulating Hormone, Serum Testosterone, Serum Prolactin, Blood sugar levels to rule out hormonal disorders.

The capsules of the present invention (E-MA-H) at a dose of 2 capsules, twice daily, with a glass of warm milk were given to all subjects for a period of 30 days. Various components of male sexual function were evaluated before treatment (Day 0), at Day 15 & Day 30.

The results in overall sexual function as measured by the IIEF (International Index of Erectile Function) questionnaire were statistically significant after 30 days of therapy ($p<0.05$). A statistically significant improvement was found in erectile dysfunction, libido, intercourse frequency, orgasm and overall satisfaction ($p<0.05$) at the end of the study as compared to baseline. The overall score on the IPE (Index of Premature Ejaculation) questionnaire and increase in IELT (Intravaginal Ejaculatory Latency Time) was statistically significant ($p<0.05$) between baseline and end of treatment (Day 30). It was observed that the males as well as the female partners were satisfied by using the treatment. All vital parameters did not show any significant change. No serious adverse events (SAE) were noted during the study period of 30 days indicating the safety of the product.

From this study it has been demonstrated both subjectively as well as objectively that E-MA-H is effective in improving the overall Quality of sexual life in males with various forms of sexual disorders. It has proven to be safe for use in humans as there were no major adverse events reported during the study. It has also been proved to be efficacious in all the parameters of sexual function like libido, Intercourse frequency, erectile dysfunction, intercourse satisfaction, orgasmic function and overall satisfaction.

Further, the inventors have elaborately investigated the performance of the compositions of the present invention by conducting a triple blind, randomized, double dummy, prospective placebo controlled, dose determination study.

The safety and efficacy of E-MA-H and E-MA-HP capsules (at two different doses) in subjects with male sexual dysfunction (Erectile Dysfunction and/or low libido and sexual dissatisfaction and/or premature ejaculation) was evaluated as per Intention to treat [ITT] and Per Protocol [PP] Analysis.

Analysis for evaluation of safety was done on an ITT data set of 147 subjects. Analysis of efficacy was conducted in both ITT and PP populations. In the overall assessment of efficacy variables International Index of Erectile Function IIEF-A, IIEF-B, IIEF (A+B) and Index for Premature Ejaculation, IPE; no. of subjects analyzed was 147 in the ITT and 124 in the PP population.

Results:

Efficacy Result— i. Treatment with E-MA-H (low and high dose) and E-MA-HP resulted in a statistically significant increase of IIEF-A (used to measure Erectile Function), IIEF-B (used measure other Sexual Dysfunctions besides erectile dysfunction and premature ejaculation) and IPE (which is used to assess Premature Ejaculation) scores versus treatment with placebo, in subjects with male sexual dysfunction. No significant difference in effect, existed between the active treatment groups.

ii. E-MA-H (low and high dose) and E-MA-HP demonstrated a statistically significant effect as compared to placebo, in enhancing erectile function in subgroup of subjects with predominant erectile dysfunction and in improving ejaculatory control in subgroup of subjects predominantly affected by premature ejaculation. The active treatments and placebo did not exhibit any significant effect in subgroup of subjects with other forms of sexual dysfunction like diminished libido or low sexual satisfaction.

iii. Significantly more number of subjects in the active treatment groups were satisfied and wanted to continue treatment as compared to those in the placebo group. Global assessment by investigator yielded significantly higher number of satisfactory responses for the active therapies as compared to placebo.

Safety Result— i. E-MA-H (low and high dose) and E-MA-HP were well tolerated in subjects with sexual dysfunction. No serious adverse event occurred during the entire study. Incidence of adverse events was comparable across groups. Gastrointestinal side effects of flatulence and acidity were commonly reported in all groups. There was no clinically significant change in vital parameters, ECG findings, urine analysis and other laboratory parameters in any of the treatment groups. None of the subjects from the active treatment groups were withdrawn due to adverse events.

Conclusion:—

In a nut shell, the inventive formulations were successful in statistically differentiating the treatment effect from the "placebo effect". Results obtained on analysis by INTENTION-TO-TREAT corresponded with those on analysis by PER-PROTOCOL. Moreover, the responses to the questionnaires were corroborated in the global assessments done by the investigator and the opinions of the subjects. Overall, the efficacy and safety results of the study have provided proof of the beneficial role of the active ingredients.

The present invention will be further illustrated by the following examples which are not to be construed to limit the scope thereof.

Example 1

Each capsule of the present invention comprising following ingredients: [E-MA-H]

| Ingredients | Extracts (mg/caps) | Parts used | Solvent |
|---|---|---|---|
| Tribulus terrestris | 50 | Fruit | Alcohol 85% |
| Withania somnifera | 120 | Roots/Rhizomes | Hydro Alcoholic 50% |
| Asparagus adscendens | 100 | Roots/Rhizomes | Water |
| Mucuna pruriens | 50 | Seed | Water |
| Asteracantha longifolia | 40 | Entire plant | Water |
| Curculigo orchioides | 50 | Roots/Rhizomes | Water |
| Asphaltum | 75 | Exudate | Hydro Alcoholic 50% |

Example 2

Each capsule of the present invention comprising following ingredients [E-MA-HP]

| Ingredients | Extracts (mg/caps) | Part used | Solvent |
|---|---|---|---|
| Tribulus terrestris | 50 | Fruit | Alcohol 85% |
| Withania somnifera | 120 | Roots/Rhizomes | Hydro Alcoholic 50% |
| Asparagus adscendens | 100 | Roots/Rhizomes | Water |
| Mucuna pruriens | 50 | Seed | Water |
| Asteracantha longifolia | 40 | Entire plant | Water |
| Curculigo orchioides | 50 | Roots/Rhizomes | Water |
| Asphaltum | 75 | Exudate | Hydro Alcoholic 50% |
| Anacyclus pyrethrum | 25 | Root | Alcohol 70% |
| Piper longum | 10 | Fruit | Alcohol 90% |

The present invention encompasses the combination of the above herbal ingredients in the ranges specified in the specification. Although the present invention has been described hereinabove by way of an illustrative embodiment thereof, this embodiment can be modified at will without departing from the spirit and nature of the subject invention. It will further be apparent now to a person of ordinary skill in the art that a large number of permutations and combinations are possible with provision of the above features.

Example 3

Effect of E-MA-H and E-MA-HP in Male Patients with Sexual Dysfunction: A Triple Blind, Randomized, Double Dummy, Prospective Placebo Controlled, Dose Determination Study The study was undertaken to evaluate the safety and efficacy of two dietary supplements E-MA-H (at two different doses) and E-MA-HP [having formulation as described in Example 1 and 2 respectively] in subjects with male sexual dysfunction (Erectile Dysfunction and/or low libido and sexual dissatisfaction and/or premature ejaculation). Further, as a secondary objective change in testosterone levels; safety and tolerability of E-MA-H and E-MA-HP capsules as a dietary supplement for male sexual health and determination of best dose of E-MA-H for male sexual health along with the determination of onset of action of E-MA-H and E-MA-HP were evaluated.

Dosage Regimen and Quantitative Description:—

The investigational products were self administered by the subjects with a glass of warm milk. Following was the dosage regimen in 4 different groups;

Group I—Placebo 2 capsules twice a day for 2 months

Group II—E-MA-H (low dose) 2 capsules at night for 2 months

Group III—E-MA-H (high dose) 2 capsules twice a day for 1 month and then 2 capsules at night for the next month.

Group IV—E-MA-HP 2 capsules twice a day for 2 months

According to the most predominant condition of sexual dysfunction, each group was further classified into 3 subgroups as follows:

Subgroup 1—Subjects primarily suffering from erectile dysfunction

Subgroup 2—Subjects primarily suffering from premature ejaculation

Figure 6:
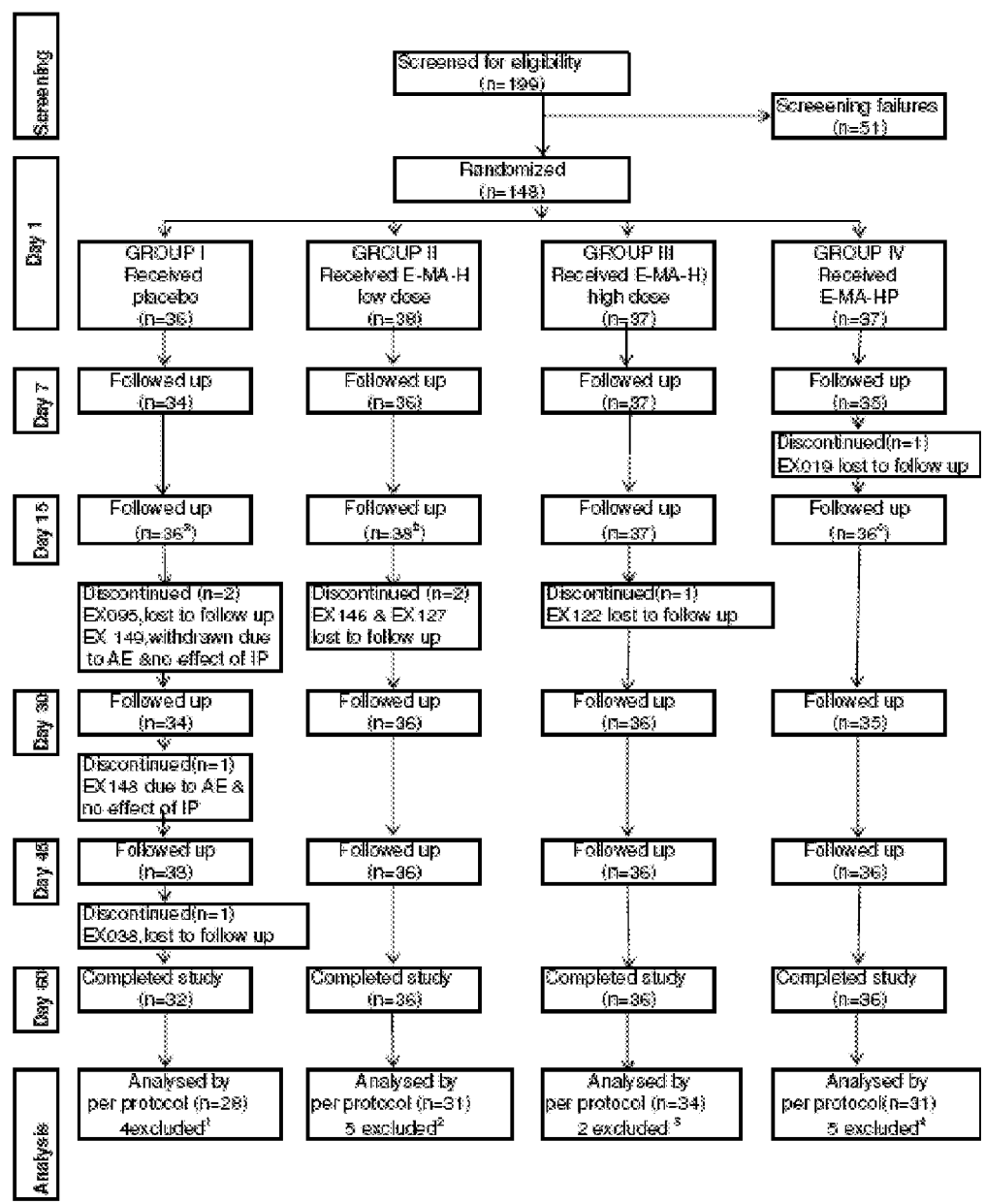
FIG. 6: is a chart outlining the treatment regimen for groups used in the current study

Subgroup 3—Subjects primarily suffering from sexual dysfunction other than ED and PE viz loss of libido, sexual dissatisfaction etc The treatment regimen for each group is outlined in FIG. 6.

Experimental Design:—

148 Patients were recruited in the trial out of which 140 completed the study.

Data Sets Analyzed:—

Analysis was performed for two types of population

ITT (Intention-To-Treat):—ITT population included subjects who were administered at least a single dose and for whom at least a single post-baseline assessment was available. Last observation carried forward (LOCF) technique was used to account for missing data.

AND

PP (per protocol):—PP population included subjects who complied with the treatment regimen and assessments schedule strictly as per the protocol.

Efficacy Variables:

Primary efficacy variables tested were International Index of Erectile Function (IIEF), Index for Premature Ejaculation (IPE) questionnaires & IELT (Intravaginal Ejaculatory Latency Time). While secondary efficacy variables tested were EDITS (Erectile Dysfunction inventory for treatment satisfaction), Serum testosterone levels and days for onset of action. The International Index of Erectile Function (IIEF) is an instrument for measuring erectile dysfunction. It is used to monitor response to the treatment. In the present study at each visit investigator/coordinator had administered each question to the subject and noted down the response. The part "A" of IIEF was used to measure erectile dysfunction. Part "B" was used to measure other sexual dysfunction except premature ejaculation & erectile dysfunction. IPE is an instrument for measuring Premature Ejaculation.

Observation and Conclusion:

The following observation was made in the study:

1) Vital parameters (pulse, systolic and diastolic blood pressure and respiration rate), Haematological and Biochemical Parameters, ECG changes, urine analyses and tolerability assessment was carried and no clinically significant changes were seen in any of the groups at the end of the study period.
2) No serious adverse event occurred during the treatment duration signifying the safety of the products. Two subjects receiving placebo were withdrawn from the study by the investigator, due to mild abdominal pain occurring in one, and oedema with pain in lower extremities in the other.
3) E-MA-H (low and high dose) and E-MA-HP recorded a significant improvement of IIEF (A) scores [Table 1]; IIEF (B) scores [Table 2] and IIEF (A+B) scores [Table 3] used for assessment of erectile function as compared to placebo. In other words, the overall quality of erectile function was enhanced with an increase in ability to achieve and maintain erections sufficient for satisfactory sexual activity.

TABLE 1

Effect on IIEF-A scores (overall analysis in ITT population)

| IIEF-A | Baseline | Day 7 | Day 15 | Day 30 | Day 45 | Day 60 |
|---|---|---|---|---|---|---|
| Gr. I (n = 36) | 17.69 ± 3.27 | 18.63 ± 3.78 | 19.38 ± 4.35 | 20.08 ± 4.31 | 20.58 ± 4.56 | 20.75 ± 4.95 |
| Gr. II (n = 38) | 18.15 ± 5.17 | 19.36 ± 4.78 | 21.28 ± 4.65 | 22.94 ± 4.33* | 24.07 ± 4.71* | 24.86 ± 5.0** |
| Gr. III (n = 37) | 19.45 ± 3.67 | 19.86 ± 3.96 | 21.45 ± 3.47 | 22.72 ± 3.25 | 24.75 ± 3.73 | 25.45* ± 3.77 |
| Gr. IV (n = 36) | 17.61 ± 4.48 | 18.88 ± 4.58 | 21.11 ± 4.96 | 22.27 ± 5.37 | 23.58 ± 4.97* | 25.25 ± 4.29** |

*$p < 0.05$,
**$p < 0.01$ for change in mean score from baseline as compared to placebo, using ANOVA and Scheffe's test. IIEF-A data is expressed as mean ± SD

TABLE 2

Effect on IIEF-B scores (overall analysis in ITT population)

| IIEF-B | Baseline | Day 7 | Day 15 | Day 30 | Day 45 | Day 60 |
|---|---|---|---|---|---|---|
| Gr. I (n = 35) | 27.44 ± 4.64 | 27.9 ± 4.52 | 29.5 ± 5.65 | 30.25 ± 5.08 | 31.02 ± 5.38 | 31.16 ± 5.82 |
| Gr. II (n = 38) | 26.31 ± 5.13 | 27.63 ± 5.43 | 30.02 ± 4.97 | 33.15 ± 4.98** | 34.86 ± 5.66** | 35.84 ± 5.80** |
| Gr. III (n = 37) | 26.97 ± 4.54 | 27.75 ± 6.18 | 29.97 ± 3.67 | 32.27 ± 4.44 | 34.56 ± 4.83* | 36.29 ± 4.71** |
| Gr. IV (n = 36) | 26.97 ± 5.08 | 28.75 ± 4.99 | 31.22 ± 5.60 | 33.33 ± 5.74** | 35.22 ± 4.71** | 37.52 ± 4.56** |

*$p < 0.05$,
**$p < 0.01$ for change in mean score from baseline as compared to placebo, using ANOVA and Scheffe's test IIEF-B Data is expressed as mean ± SD

TABLE 3

Effect on IIEF-(A + B) scores in ITT

| IIEF (A + B) | Baseline | Day 7 | Day 15 | Day 30 | Day 45 | Day 60 |
|---|---|---|---|---|---|---|
| Gr. I (n = 36) | 45.13 ± 6.68 | 46.72 ± 7.13 | 48.86 ± 9.19 | 50.74 ± 8.01 | 52.22 ± 8.70 | 52.51 ± 9.67 |
| Gr. II (n = 38) | 44.42 ± 8.72 | 47.28 ± 8.69 | 50.78 ± 8.76 | 55.78 ± 8.88** | 58.55 ± 10.05** | 60.71 ± 10.47** |

TABLE 3-continued

Effect on IIEF-(A + B) scores in ITT

| IIEF (A + B) | Baseline | Day 7 | Day 15 | Day 30 | Day 45 | Day 60 |
|---|---|---|---|---|---|---|
| Gr. III (n = 37) | 46.40 ± 6.58 | 47.78 ± 6.54 | 51.29 ± 6.10 | 54.89 ± 6.86 | 59.37 ± 8.04* | 61.81 ± 7.92** |
| Gr. IV (n = 36) | 44.08 ± 8.44 | 47.08 ± 9.03 | 51.97 ± 9.74 | 55.25 ± 10.79** | 58.5 ± 9.82** | 62.63 ± 9.17** |

*$p < 0.05$,
**$p < 0.01$ is for change in mean score from baseline as compared to placebo, using ANOVA and Scheff test. IIEF(A + B) data is expressed as mean ± SD 4) Subjects receiving E-MA-H (low/high dose) and E-MA-HP experienced a remarkable improvement in sexual function with respect to intercourse satisfaction; sexual desire and overall satisfaction when compared to placebo. E-MA-H (both doses) and E-MA-HP were also effective in the treatment of premature ejaculation. The IPE scores for premature ejaculation [Table 4] were significantly high in these groups compared to those noticed in the placebo group.

TABLE 4

Effect on IPE scores (overall analysis in ITT population)

| IPE | Baseline | Day 7 | Day 15 | Day 30 | Day 45 | Day 60 |
|---|---|---|---|---|---|---|
| Gr. I (n = 36) | 26.47 ± 6.20 | 27.19 ± 6.20 | 28.5 ± 6.61 | 29.42 ± 5.97 | 30.17 ± 6.93 | 30.85 ± 7.24 |
| Gr. II (n = 38) | 27.18 ± 5.79 | 28.89 ± 4.95 | 31.73 ± 5.21 | 34.76 ± 6.33** | 35.65 ± 6.65** | 36.86 ± 7.23** |
| Gr. III (n = 37) | 27.40 ± 5.00 | 28.51 ± 4.57 | 30.89 ± 4.24 | 33.54 ± 4.80 | 36.54 ± 5.72** | 37.67 ± 5.55** |
| Gr. IV (n = 36) | 26.88 ± 5.93 | 28.91 ± 5.23 | 31.38 ± 5.74 | 33.88 ± 5.95** | 35.72 ± 5.96** | 38.25 ± 5.77** |

*$p < 0.05$,
**$p < 0.01$ for change in mean score from baseline as compared to placebo, using ANOVA and Scheff test. IPE Data is expressed as mean ± SD 5) For a majority of efficacy parameters, E-MA-H low dose therapy produced consistently faster results as seen on Day 30. Although a difference existed in the efficacy responses of the two doses of E-MA-H, it did not approach a significant level throughout the study.
6) In the overall analysis, the efficacy of the dietary supplements E-MA-H (at both doses) and E-MA-HP in male sexual dysfunction was established in a broader view, irrespective of the predominance of a specific condition. Focus of the subgroup analysis was to ascertain the efficacy of these dietary supplements in subjects with predominance of a specific condition (ED, PE, other than ED or PE) of sexual dysfunction. Results from the subgroup analysis reinforced those obtained from the overall analysis except for significant improvement of IIEF-B scores which was lacking in subjects of subgroup 3 which may be due to inadequate sample size in subgroup 3.
7) Overall satisfaction with treatment as assessed by the EDITS questionnaire was high in subjects treated with EMAH (low/highdose) or E-MA-HP than in those receiving placebo [Table 5]. This was better demonstrated in subjects than in their female partners possibly due to lack of adequate sample size data in the latter.

TABLE 5

EDITS data from subjects-male version (ITT)

| EDITS | Day 30 | Day 60 |
|---|---|---|
| Group I (n = 34) | 51.23 ± 21.78 | 54 ± 24.79 |
| Group II (n = 36) | 70.88 ± 15.67** | 78.55 ± 18.27** |
| Group III (n = 36) | 65.61 ± 13.99* | 75.83 ± 15.36** |
| Group IV (n = 36) | 65.55 ± 22.19* | 73.16 ± 21.07** |

*$p < 0.05$,
**$p < 0.01$ compared to placebo, using ANOVA and Scheff test. Data is expressed as mean ± SD 8) In the global assessment of therapy by investigator, treatment with E-MA-H (at either dose) and E-MA-HP clearly emerged as the preferred choices of treatment over placebo. A larger proportion of patients in the active treatment groups as compared to that in the placebo, desired to continue therapy. This further emphasizes the overall effectiveness of E-MA-H and E-MA-HP in addressing sexual dysfunction.
9) Sexual disorders in males, especially erectile dysfunction and decreased libido, have often been investigated for their relationship with testosterone—the male hormone. In the present study, however, no correlation could be elucidated between serum testosterone levels and the efficacy results of the active treatments as evidenced from table 6. It can be therefore inferred that the efficacy of E-MA-H and E-MA-HP is not due to a testosterone mediated mechanism.

TABLE 6

Effect on serum testosterone (ITT)

| | Baseline | Day 30 | Day 60 |
|---|---|---|---|
| Group I (n = 36) | 538.23 ± 204.41 | 497.71 ± 191.43 | 529.75 ± 205.18 |
| Group II (n = 38) | 553.13 ± 212.37 | 500.10 ± 221.22 | 507.37 ± 189.07 |
| Group III (n = 37) | 579.10 ± 174.04 | 466.61 ± 195.12 | 477.11 ± 173.35 |
| Group IV (n = 37) | 513.44 ± 147.89 | 452.92 ± 164.95 | 480.57 ± 191.18 |

S. testosterone data is expressed as mean ± SD

From the foregoing discussion it is evident that E-MA-HP and both doses of E-MA-H are effective, safe and tolerable in the subjects with sexual dysfunction. They have a wide application in a range of conditions like erectile dysfunction, premature ejaculation and loss of libido which are commonly occurring forms of male sexual dysfunction. However, there is no significant difference among E-MA-H & E-MA-HP.

Thus the synergistic compositions of the present invention hold promise as a complete, safe, effective and well-tolerated herbal formulation for male sexual dysfuntion.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

We claim:

1. An oral dosage form comprising an effective amount of a herbal composition for the treatment of erectile dysfunction or premature ejaculation, said herbal composition comprising:
   a) an 85% alcohol extract of a fruit of *Tribulus terrestris*;
   b) a 50% alcohol extract of a root or rhizome of *Withania somnifera*;
   c) an extract of *Curculigo orchioides*;
   d) an extract of *Mucuna pruriens*;
   e) an extract of *Asparagus adscendens*;
   f) an extract of *Asteracantha longifolia*;
   g) a 50% alcohol extract of *Asphaltum* exudate;
   h) optionally, an extract of *Piper longum*; and
   i) optionally, an extract of *Anacyclus pyrethrum*;
      wherein the oral dosage form is a capsule or a tablet.

2. The herbal composition as claimed in claim 1, wherein the extracts of *Curculigo orchioides; Mucuna pruriens; Asparagus adscendens*; and *Asteracantha longifolia* in the herbal composition are derived from fruit, leaves, flower heads, stem, bark, or root of the corresponding herb.

3. The herbal composition as claimed in claim 2, wherein the extracts of *Curculigo orchioides; Mucuna pruriens; Asparagus adscendens*; and *Asteracantha longifolia* in the herbal composition is extracted using a solvent selected from the group consisting of water, an organic solvent, and a mixture thereof.

4. The herbal composition as claimed in claim 2, wherein the extracts of *Curculigo orchioides; Mucuna pruriens; Asparagus adscendens*; and *Asteracantha longifolia* in the herbal composition are extracted using a solvent selected from the group consisting of water, alcohols and hydro-alcohols.

5. An oral dosage form comprising an effective amount of a herbal composition for the treatment of erectile dysfunction or premature ejaculation, said herbal composition comprising:
   a) an 85% alcohol extract of *Tribulus terrestris* fruit in an amount of about 10 to 90% of the total formulation;
   b) a 50% alcohol extract of *Withania somnifera* root, *Withania somnifera* rhizome, or a mixture thereof, in an amount of about 10 to 90% of the total formulation;
   c) a *Curculigo orchioides* root extract, *Curculigo orchioides* rhizome extract, or a mixture thereof, in an amount of about 10 to 90% of the total formulation;
   d) a *Mucuna pruriens* seed in an amount of about 5 to 70% of the total formulation,
   e) an *Asparagus adscendens* root extract, *Asparagus adscendens* rhizome extract, or a mixture thereof, in an amount of about 10 to 90% of the total formulation;
   f) an *Asteracantha longifolia* plant extract in an amount of about 5 to 90% of the total formulation;
   g) a 50% alcohol extract of *Asphaltum* exudate in an amount of about 10 to 90% of the total formulation;
   h) a *Piper longum* fruit extract in an amount of about 0 to 70% of the total formulation; and
   i) an *Anacyclus pyrethrum* root extract in an amount of about 0 to 70% of the total formulation,
      wherein the oral dosage form is a capsule or a tablet.

6. The herbal composition as claimed in claim 5, wherein said composition comprises at least one pharmaceutical excipient selected from the group consisting of binders, diluents, lubricants, disintegrants, pharmaceutical oils and bases, and mixtures thereof.

7. A method for treating symptoms associated with male sexual dysfunction or improving sexual function in a male, comprising a step of administering a composition to said male, wherein said composition comprises:
   a) an 85% alcohol extract of *Tribulus terrestris* fruit in an amount of about 10 to 90% of the total formulation;
   b) a 50% alcohol extract of *Withania somnifera* root, *Withania somnifera* rhizome, or a mixture thereof, in an amount of about 10 to 90% of the total formulation;
   c) a *Curculigo orchioides* root extract, *Curculigo orchioides* rhizome extract, or a mixture thereof, in an amount of about 10 to 90% of the total formulation;
   d) a *Mucuna pruriens* seed extract in an amount of about 5 to 70% of the total formulation,
   e) an *Asparagus adscendens* root extract, *Asparagus adscendens* rhizome extract, or a mixture thereof, in an amount of about 10 to 90% of the total formulation;
   f) an *Asteracantha longifolia* plant extract in an amount of about 5 to 90% of the total formulation;
   g) a 50% alcohol extract of *Asphaltum* exudate in an amount of about 10 to 90% of the total formulation;
   h) a *Piper longum* fruit extract in an amount of about 0 to 70% of the total formulation; and
   i) an *Anacyclus pyrethrum* root extract in an amount of about 0 to 70% of the total formulation.

8. The method as claimed in claim 7, wherein said male is human.

9. A method for treating a symptom associated with erectile dysfunction and premature ejaculation in a subject suffering symptoms associated with Male Sexual Dysfunction, wherein said method comprises administering an effective amount of a herbal composition to the subject, said herbal composition comprising:
 a) an 85% alcohol extract of a fruit of *Tribulus terrestris* in an amount of about 10 to 90% of the total formulation;
 b) a 50% alcohol extract of a root or rhizome of *Withania somnifera* in an amount of about 10 to 90% of the total formulation;
 c) an extract of *Curculigo orchioides*;
 d) an extract of *Mucuna pruriens*;
 e) an extract of *Asparagus adscendens*;
 f) an extract of *Asteracantha longifolia*;
 g) a 50% alcohol extract of *Asphaltum* exudate in an amount of about 10 to 90% of the total formulation;
 h) optionally, an extract of *Piper longum*; and
 i) optionally, an extract of *Anacyclus pyrethrum*.

10. A method for treating a symptom associated with erectile dysfunction and premature ejaculation as claimed in claim 9, wherein said symptom is erectile dysfunction, premature ejaculation, sexual dissatisfaction, loss of libido, loss of orgasmic function, or a combination thereof.

11. The method as claimed in claim 9, wherein said subject is human.

12. The method as claimed in claim 9, wherein:
 the *Curculigo orchioides* extract is a water extract;
 the *Mucuna pruriens* extract is a water extract;
 the *Asparagus adscendens* extract is a water extract; and
 the *Asteracantha longifolia* extract is a water extract.

13. The method as claimed in claim 9, wherein:
 the *Piper longum* extract is an alcohol or hydroalcoholic extract; and the *Anacyclus pyrethrum* extract is an alcohol or hydroalcoholic extract.

14. The method as claimed in claim 9, wherein said herbal composition includes:
 the *Curculigo orchioides* extract in an amount of about 10 to 90% of the total formulation;
 the *Mucuna pruriens* extract in an amount of about 5 to 70% of the total formulation;
 the *Asparagus adscendens* extract in an amount of about 10 to 90% of the total formulation; and
 the *Asteracantha longifolia* extract in an amount of about 5 to 90% of the total formulation.

15. A method for treating erectile dysfunction or premature ejaculation in a subject, wherein said method comprises administering an effective amount of a herbal composition to the subject, said herbal composition comprising:
 a) an 85% alcohol extract of a fruit of *Tribulus terrestris*;
 b) a 50% alcohol extract of a root or rhizome of *Withania somnifera*;
 c) an extract of *Curculigo orchioides*;
 d) an extract of *Mucuna pruriens*;
 e) an extract of *Asparagus adscendens*;
 f) extracts of *Asteracantha longifolia*;
 g) a 50% alcohol extract of *Asphaltum* exudate;
 h) optionally, an extract of *Piper longum*; and
 i) optionally, an extract of *Anacyclus pyrethrum*.

16. The method as claimed in claim 15, wherein said subject is human.

* * * * *